United States Patent [19]

Hall et al.

[11] 4,131,555

[45] * Dec. 26, 1978

[54] DETERGENT COMPOSITION

[75] Inventors: John B. Hall, Rumson; Wilhelmus J. Weigers, Red Bank, both of N.J.

[73] Assignee: International Flavors & Fragrances Inc., New York, N.Y.

[*] Notice: The portion of the term of this patent subsequent to Dec. 26, 1995, has been disclaimed.

[21] Appl. No.: 847,209

[22] Filed: Oct. 31, 1977

Related U.S. Application Data

[63] Continuation-in-part of Ser. No. 753,618, Dec. 22, 1976, Pat. No. 4,061,686, which is a continuation-in-part of Ser. No. 662,818, Mar. 1, 1976, Pat. No. 4,014,944.

[51] Int. Cl.$^2$ ............................................... C11D 3/50
[52] U.S. Cl. ................................ 252/89 R; 252/522; 252/539; 252/540
[58] Field of Search ............... 252/89, 132, 135, 522, 252/539, 540

[56] References Cited

U.S. PATENT DOCUMENTS

| | | | |
|---|---|---|---|
| 3,499,937 | 3/1970 | Dorsky et al. | 260/631 |
| 4,026,824 | 5/1977 | Pittet et al. | 252/89 |
| 4,031,140 | 6/1977 | Schreiber et al. | 252/89 |
| 4,036,774 | 7/1977 | Ouwerkerk et al. | 252/89 |
| 4,041,084 | 8/1977 | Light et al. | 252/89 |

FOREIGN PATENT DOCUMENTS 876241  5/1953  Fed. Rep. of Germany ........... 260/631

*Primary Examiner*—Mayer Weinblatt
*Attorney, Agent, or Firm*—Arthur L. Liberman; Franklin D. Wolffe; Harold Haidt

[57] ABSTRACT

Described is a detergent composition containing as a key ingredient, a mixture of compounds having a sandalwood aroma produced according to a process which comprises:
(1) Reacting catechol with camphene in the presence of a Friedel Crafts Catalyst to form a first alkylation product; and then
(2) Treating said first alkylation product with hydrogen in the presence of a hydrogenation catalyst, thus forming, initially, diol intermediates and then, on continuing the hydrogenation, the mixture useful in the perfume compositions of our invention.

2 Claims, 6 Drawing Figures

EXAMPLE XIII
GLC PROFILE, STARTING MATERIAL

EXAMPLE XIII

GLC PROFILE
RESULT OF THE FIRST STAGE OF HYDROGENATION

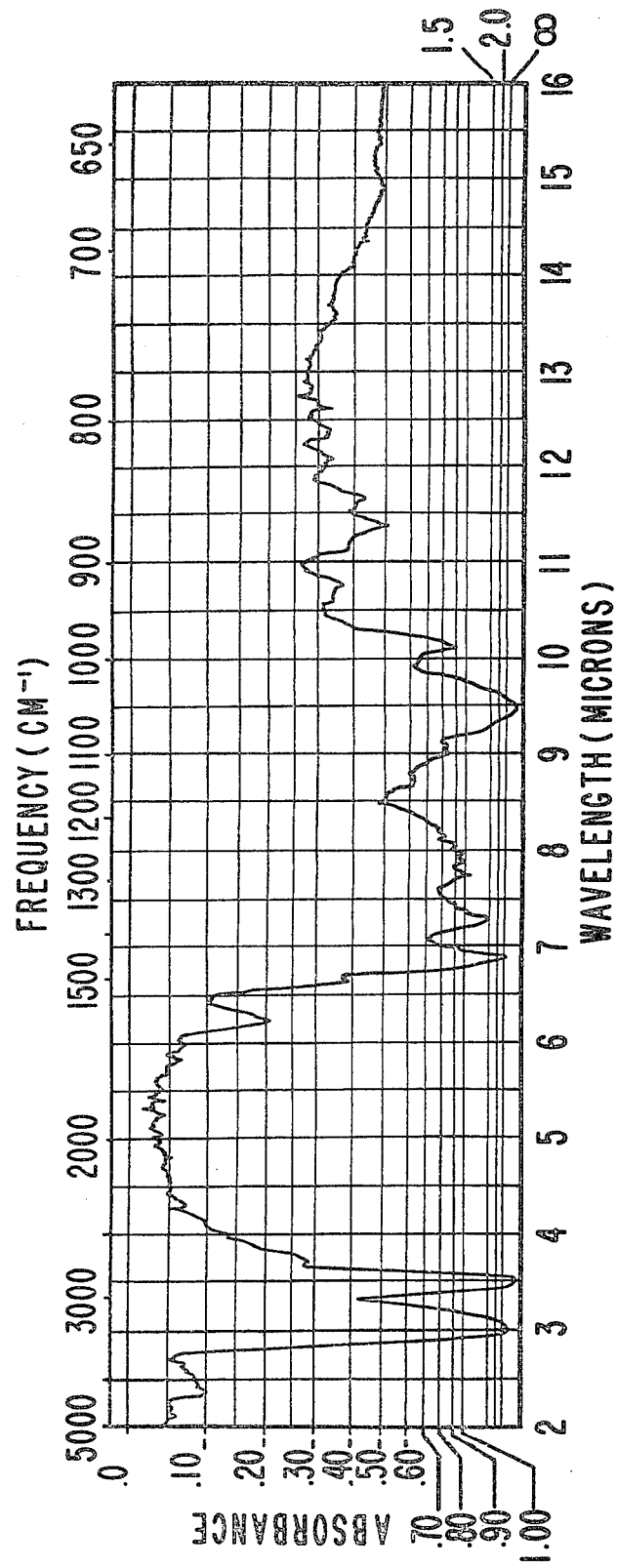
FIG. 4-A
INFRA RED SPECTRUM FOR EXAMPLE XIII DIOL INTERMEDIATE RESULT OF FIRST STAGE OF HYDROGENATION

EXAMPLE XIII

GLC PROFILE FINAL PRODUCT
RESULT OF SECOND STAGE OF HYDROGENATION

DETERGENT COMPOSITION

This application is a continuation-in-part of U.S. patent application Ser. No. 753,618, filed on Dec. 22, 1976 now U.S. Pat. No. 4,061,686 issued on Dec. 6, 1977, which, in turn, is a continuation-in-part of U.S. patent application Ser. No. 662,818, filed on Mar. 1, 1976, now U.S. Pat. No. 4,014,944, issued on Mar. 29, 1977.

BACKGROUND OF THE INVENTION

The present invention relates to novel detergent compositions which contain as key ingredients a mixture which gives rise to an intense sandalwood aroma.

In perfumery, perhaps the most desired of the popular wood notes, as well as the most expensive and least available, is the sandalwood odor. Oil of sandalwood, therefore, while being highly prized in the perfume world because of its desirable odor, has enjoyed only limited use, on account of its limited availability and high cost.

In the past, efforts have been made to produce synthetic substitutes for the natural oil of sandalwood, but they have met with limited success. One of the products heretofore known is the chemical, 1-oxy-2-methoxy-4-camphylcyclohexane, also sometimes referred to as isobornylhexahydroguaiacol, which is described in German Patent 876,241. The formula of the aforementioned compound may be represented as follows:

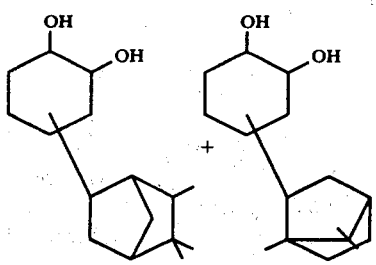

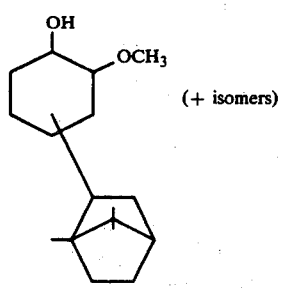

Certain Russian workers, in 1957, published an industrial method for the manufacture of this compound, isobornylhexahydroguaiacol, which they termed, Santalidol, and described it as having a fairly mild odor of the sandalwood type. L. A. Kheifits et al., Masloboino-Zhirovaya Prom 23, No. 6, 35–38 (1957); Chem. Abs., 51, 17, 107$^d$ (1957).

The process employed by Kheifits et al involves the hydrogenation of isobornylguaiacol and isomers thereof in the presence of Raney nickel at elevated temperature and pressure.

Dorsky and Easter in U.S. Pat. No. 3,499,937, issued on Mar. 10, 1970 modified the Kheifits et al process to increase the amount of hydrogen absorbed by the isobornylguaiacol and isomers thereof. The increased amount of hydrogen apparently altered the chemical nature of the product and instead of isobornylhexahydroguaiacol and isomers thereof, which contains one hydroxyl and one methoxy group, Dorsky and Easter indicated that they formed a new polycyclic alcohol having the formula $C_{16}H_{28}O$ which has one hydroxyl and no methoxyl group. The methoxyl group apparently was removed by hydrogenolysis. Dorsky and Easter reported that the process of U.S. Pat. No. 3,499,937 created a material possessing a strong, sandalwood-type odor. U.S. Pat. No. 3,499,937 stated that the polycyclic alcohol thus prepared is a viscous, colorless oil with a strong sandalwood-type odor having the formula:

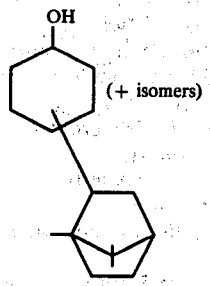

In accordance with the Dorsky and Easter process, a material is hydrogenated having the formula:

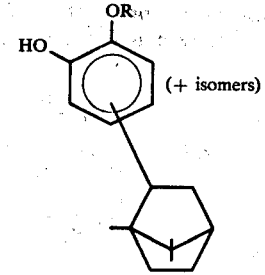

where R is a lower aliphatic hydrocarbon radical having up to 5 carbon atoms, an aromatic or a cycloaliphatic hydrocarbon radical having up to 2 carbon atoms in the side chain, in the presence of a nickel hydrogenating catalyst or copper chromite at an elevated temperature and pressure, until at least 3.5 moles of hydrogen per mole of said material have been absorbed.

At column 3, lines 35–40 Dorsky and Easter state that temperatures between about 140° C. and 250° C., and pressures above 250 pounds per square inch give satisfactory results, but that preferably temperatures within the range of 175° C. and 200° C. and pressures of from about 400 up to about 1000 pounds per square inch are used.

Swiss Pat. No. 423,058 (Demole), issued on Apr. 29, 1967, teaches that the odor of the mixture of isomers having the structure:

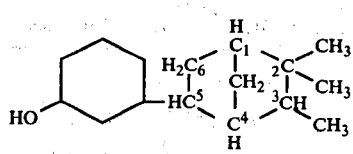

is due to a stereoisomer having the configuration:

The above-mentioned stereoisomer is taught to be prepared by condensing phenol with camphene in the presence of boron trifluoride at a temperature of 100° C. to form a terpenyl phenol mixture; then treating the terpenyl phenyl mixture with ozone thus forming a mixture of terpenyl carboxylic acids; purifying the mixture of terpenyl carboxylic acids and then carrying out a complicated sequence of reaction steps forming the desired stereoisomer product, to wit:

1. Preparation of a Terpenyl Methyl Ketone Mixture;
2. Preparation of an Enamine of Trimethyl-2,2,3-Norbornyl-5-methyl ketone;
3. Preparation of Trimethyl-2,2,3-norbornyl-5-)-3-cyclohexene-2-one-1;
4. Preparation of (trimethyl-2,2,3-norbornyl-5-)-3-cyclohexenol-1; and
5. Separation of the Stereoisomer Resulting Therefrom.

However, neither the Demole Patent nor the Dorsky and Easter Patent disclose a technique for preparing the intensely powerful sandalwood material of the instant invention.

In addition, neither the Demole nor the Dorsky or Easter Patent disclose the preparation of the intermediate diol isomer mixture containing compounds having the structures:

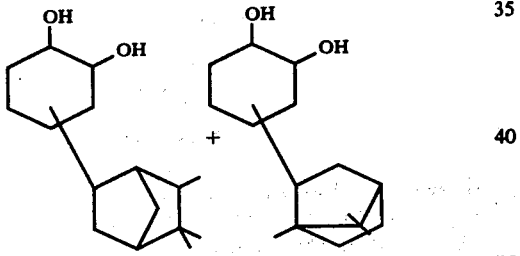

BRIEF DESCRIPTION OF THE DRAWINGS

FIG. 4a is the infra red spectrum of the diol intermediate mixture produced according to the first stage of the reaction of Example XIII.

THE INVENTION

Figure 1:
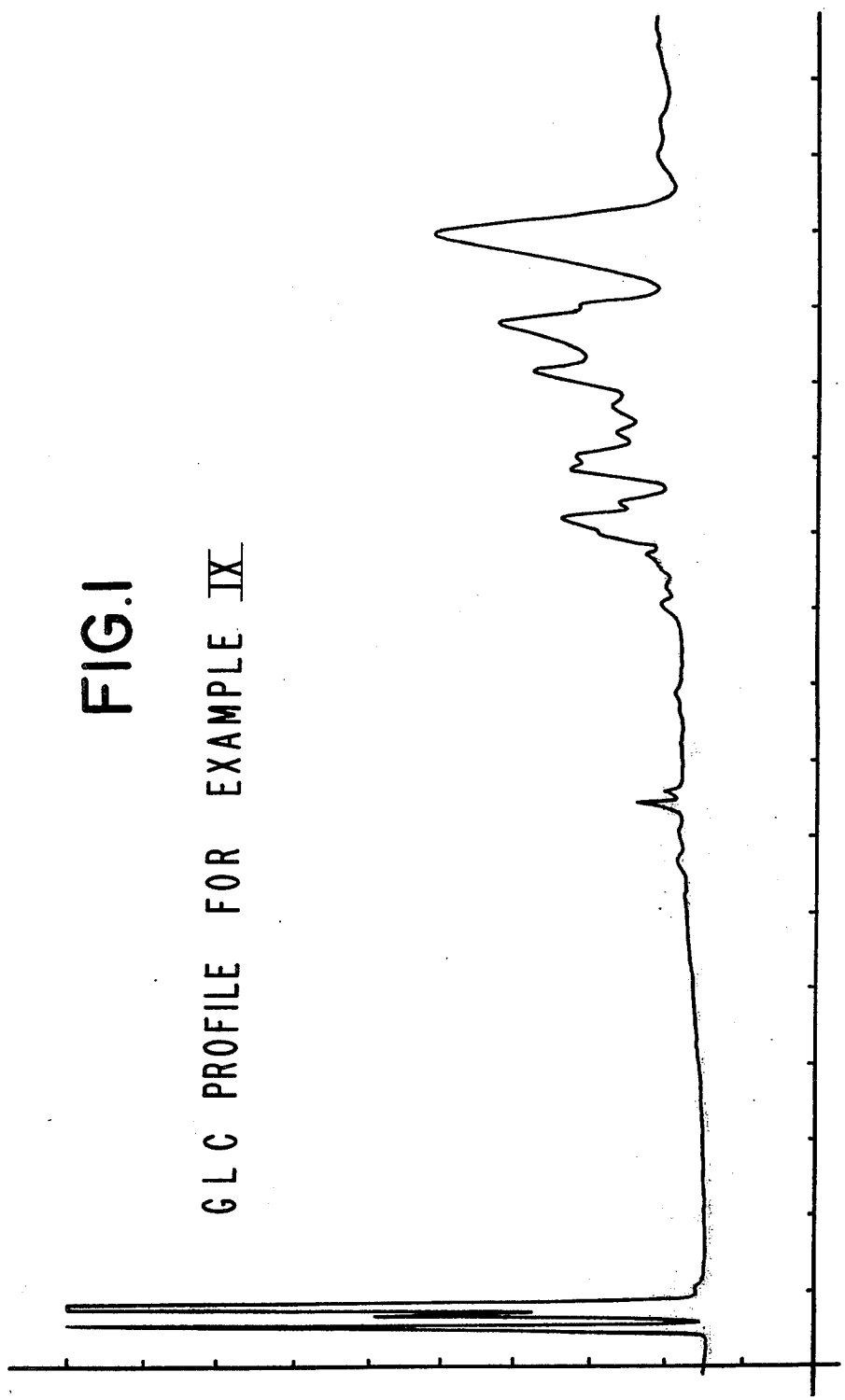
FIG. 1 is the GLC profile of the reaction product of Example IX.

The present invention relates to a novel detergent composition containing as a key ingredient a mixture having an intense sandalwood aroma prepared by a process which comprises first reacting catechol having the structure:

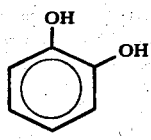

with camphene having the structure:

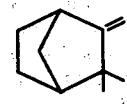

in the presence of a Friedel Crafts Catalyst and then hydrogenating the resulting mixture to first produce the novel intermediate nonodoriferous cyclohexane diols of our invention represented by the structures:

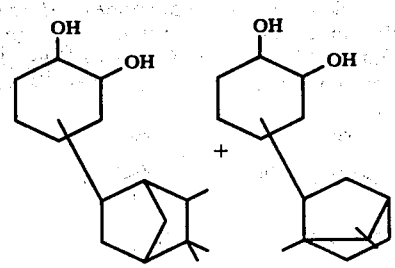

On continued hydrogenation a composition which has an intense sandalwood aroma is produced. This odoriferous composition is a mixture of compounds including compounds having the structures:

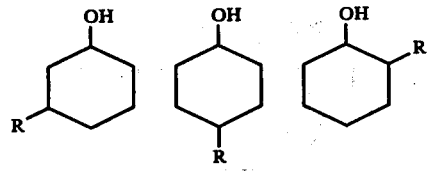

wherein the R group includes, but is not limited to, isocamphanyl and isobornyl.

The above-stated reaction sequence is summarized as follows:

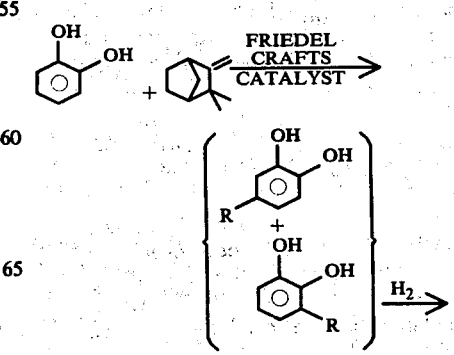

-continued

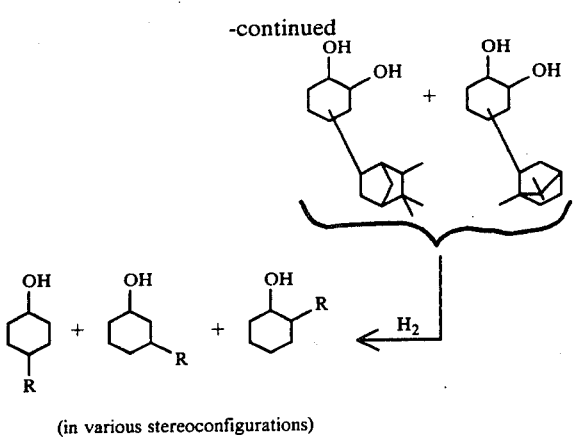

(in various stereoconfigurations)

Insofar as the reaction between camphene and catechol under the influence of the Friedel Crafts Catalyst is concerned, the following Friedel Crafts Catalysts may be employed:

Boron trifluoride etherate;
Sulfuric acid;
Acid Clay (e.g. Filtrol ®);
Molecular Sieve Catalysts (e.g. "SK-500" manufactured by the Union Carbid Company of New York, New York; a type of "Y" molecular sieve crystalline aluminosilicate catalyst);
Aluminum trichloride;
Boron trifluoride;
Boron trifluoride-acetic acid;
Boron trifluoride-phosphoric acid;
Ferric chloride; and
Zinc chloride.

Preferred catalysts are:
Acid Clay; and
Sulfuric acid.

The reaction temperature range for the reaction of catechol with camphene is from 75° C. up to about 220° C. with a preferred temperature of 120°-175° C.

The mole ratio range of catechol to camphene is from 0.5:2 up to 4:1 with a preferred mole ratio range of catechol to camphene being from about 0.8:1 up to about 1.2:1.

The ratio of Friedel Crafts Catalyst:catechol is dependent upon the particular catalyst used. Thus, when using a boron trifluoride-etherate catalyst the range used is from 2 up to 25 g of catalyst per mole of catechol, with a preferred range of from about 8 up to about 12 g catalyst per mole of catechol. When using sulfuric acid the range is from 0.05 up to about 5 g of sulfuric acid per mole of catechol with a preferred range of from about 0.1 up to about 0.5 g of sulfuric acid per mole of catechol (based upon 100% sulfuric acid). When using an acid clay such as Filtrol ®, a range of from about 2.5 g up to about 50 g of catalyst per mole of catechol is used with a preferred range of from about 8 g of acid clay up to about 15 g of acid clay per mole of catechol.

An inert solvent (that is, not reactive with either of camphene or catechol or the Friedel Crafts Catalyst) may be used for the step of reacting catechol with camphene, but it is not necessary to use such inert solvent. When it is desired to utilize the inert solvent, particularly when using a boron trifluoride-etherate catalyst, a convenient solvent is toluene; but other "inert" solvents may also be used, e.g. o-xylene, m-xylene, p-xylene and halogenated hydrocarbons such as methylene chloride, chloroform and carbon-tetrachloride.

The reaction between catechol and camphene in the presence of a Friedel Crafts Catalyst may be carried out at either atmospheric pressure, super atmospheric pressures or pressures lower than atmospheric; however, for the purposes of convenience and economy, it is preferred to carry out the reaction at atmospheric pressure.

The time of reaction of catechol with camphene is inversely proportional to the temperature of reaction. Thus, at the higher range of temperatures of reaction, shorter times of reaction are required and at the lower temperatures of reaction, longer times of reaction are required. Accordingly, the time of reaction varies from about 2 up to about 25 hours with the usual time of reaction being between 5 and 12 hours.

Insofar as the hydrogenation reaction is concerned, it may be conducted as a one-stage reaction or a two-stage reaction. When carrying out the two-stage reaction, the first stage reaction temperature is 100° C. up to 200° C.; preferably 125°-165° C. and the second stage reaction temperature is between 200° C. and 300° C.; with a preferred second stage reaction temperature range of 225°-250° C. At the end of the first stage, a nonodoriferous diol intermediate mixture claimed in parent application Ser. No. 753,618 is produced having the structures:

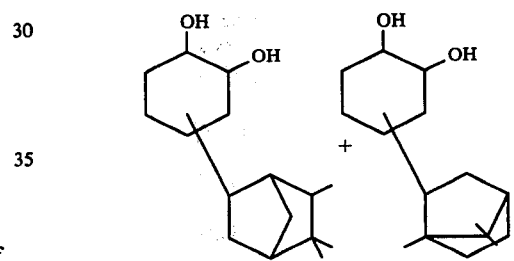

This is exemplified in Example XIII, infra. The odoriferous sandalwood composition is then produced at the higher temperature range during the carrying out of the second stage. When the process using the cyclohexane diol intermediates of our invention is carried out in one stage, the intermediate diol composition is apparently still produced in situ and as the hydrogenation proceeds this intermediate diol is converted into the odoriferous sandalwood aroma composition at the higher temperature range.

Both stages of the hydrogenation reaction may be carried out at pressures between 200 and 2500 pounds per square inch of hydrogen. When the reaction is conducted in one stage, heating is carried out whereby the reaction mass is heated directly to 200°-300° C., preferably to 225°-250° C.

The time of reaction varies inversely with the temperature and pressure of reaction with higher pressures and temperatures giving rise to a shorter required time of reaction. Accordingly, the time of reaction varies between 2 and 25 hours with the preferred time range being from about 5 up to about 15 hours.

The hydrogenation reaction may be carried out in the presence of inert solvents, (e.g. isopropyl alcohol and diisobutyl carbinol).

The ratio of solvent to camphene-catechol reaction product will thus vary from about 0 up to about 4:1 (wt/wt).

The hydrogenation is carried out in the presence of a hydrogenation catalyst, for example:
(i) Nickel catalysts such as Raney Nickel and Nickel-on-Kieselguhr;
(ii) Palladium containing catalysts such as Palladium-on-carbon
(iii) Rhodium catalysts such as Rhodium-on-carbon or Rhodium-on-Alumina;
(iv) Platinum catalysts; and
(v) Mixed Rhodium and Platinum.

More specifically, the catalysts preferred are Raney Nickel, 5% Palladium-on-carbon and 5% Rhodium-on-carbon. With regard to the use of Raney Nickel catalysts, the percent of catalyst in the camphene-catechol reaction product may vary from about 3% up to about 20% (based on weight of camphene-catechol reaction product) with a preferred percent of hydrogenation catalyst in the camphene-catechol reaction product being from about 5% up to about 10% by weight. With regard to the Palladium-on-carbon and Rhodium-on-carbon catalysts, the percent of catalyst in the reaction product may vary from about 0.1% up to about 5% (based on the total weight of camphene-catechol reaction product).

The production of the mono-hydroxy derivative from the dihydroxy or diol derivative using this hydrogenation technique is surprising, unobvious and commercially advantageous. The prior art discloses hydrogenation of phenols at high temperatures, but indicates that cyclohexyl alcohols do not form as a result of such hydrogenation. This is exemplified by the following articles:

1. Chem Abstracts 44: 3445b ("Catalytic Hydrogenation of Phenols at Higher Temperatures. II. Reduction of the isomeric di- and triphenols") Abstract of Article by Fujita, Mem. Coll. Sci. Kyoto-Imp. Univ. 23A, pp 405–20 (1942) (Shows production only of the cyclohexane diol isomers using Nickel catalyst);
2. Chem Abstracts 47: 11239b ("Alicyclic Diols"); Abstract of German Patent 857,962, issued on Dec. 4, 1952 (Discloses an improved process for preparing alicyclic diols by hydrogenating isocyclic ortho-di-hydroxy compounds in the presence of hydrogenation catalysts at elevated temperatures);
3. Chem Abstracts 52: 2912c ("Partial Dehydroxylation of Divalent Phenols by Hydrogenation"); Abstract of Czech Patent 86160 issued on Jan. 15, 1957 (Discloses the reduction of catechol using molybdenum trioxide-aluminum oxide catalyst to form phenol);
4. Chem Abstracts 53: 14058a ("Monohydric Phenols"); Abstract of German Patent 849,557 issued on Sept. 15, 1952 (Discloses production of monohydric phenols from polyhydric phenols by hydrogenation of polyhydric phenols over a zinc oxide chrome oxide catalyst);
5. Chem Abstracts 54; 22456f ("Selective Hydrogenation of the Pyrocatechols and Higher Alkyl Phenols"); Abstract of Article by Kubieka et al in Freiberger Forschungsh A131, (1960) (Discloses hydrogenation of polyhydric phenolic compositions to yield phenols using nickel sulfide, iron sulfide, copper sulfide or cobalt sulfide catalysts on alumina or silica carriers);
6. Chem Abstracts 55: 2496e ("Catalytic Hydrogenation of Hydroxybenzenes over Pt and Rh Catalysts"); Abstract by Smith et al, J. Am. Chem. Soc. 83, 2739–43 (1961) (Discloses hydrogenation of catechol over rhodium on alumina catalysts to produce 2-hydroxycyclohexanone);
7. Chem Abstracts 58: 5432f ("Coke Formation During High Temperature Hydrogenation on an Alumina-Molybdena Catalyst"); Abstract of article by Lozovoi et al in Tr. Inst. Goryuch. Isokop., Akad. Nauk. SSSR 17, pp 23–45 (1962) (Discloses hydrogenation of catechol over a molybdenum oxide-alumina catalyst at very high temperatures [515° C.]);
8. Chem Abstracts 62: 5120f ("High-Pressure Hydrogenation of Catechols in the Liquid Phase-Influence of the Quality of the Diluent and the Circulation of Products"); Abstract of article by Svajgl. Sb. Praci Vyzkumu Chem. Vyuzili Uhli. Dehtu Ropy, No. 2, pp 21–35 (1962) (Discloses hydrogenation of catechol using ferrous hydroxide on activated charcoal catalyst to yield phenol);
9. Chem Abstracts 63: 16188b ("Stereochemistry of the Catalytic Hydrogenation of Dihydroxybenzene Derivatives"); Abstract of article by Zymalkowski et al, Arch. Pharm. 298(9), pp 604–12 (1965) (Discloses the formation of cis and trans cyclohexane diols by hydrogenation of divalent phenols using rhodium on alumina and rhodium-platinum mixed catalysts).

The odoriferous mixtures thus produced as disclosed herein can be incorporated into a wide variety of finished perfume compounds and components for finished perfume compounds. It has been found that the materials produced using the intermediates of this invention have persistent fragrances as more fully described below which adapts them for incorporation into perfume compositions where a distinct sandalwood, woody musky aroma is required. To make a sandalwood type of perfume, the material produced using the intermediates of our invention can be combined with many types of odor materials, such as alcohols, hydrocarbons (e.g. sesquiterpenes), aldehydes, nitriles, esters, lactones and natural essential oils. These materials may be admixed with the product produced using the intermediates of our invention so that the combined odors of the individual components produce a pleasant and desired fragrance, particularly and preferably in sandalwood fragrances. Such perfume compositions usually contain (a) the main note or the bouquet or foundation stone of the compositions; (b) modifiers which round off and accompany the main notes; (c) fixatives which include (i) odorous substances which lend a particular note to the perfume throughout all stages of the evaporation and (ii) substances which retard evaporations; and (ii) top notes which are usually low boiling fresh smelling materials.

In perfume compositions, it is the individual components which contribute to a particular olfactory characteristic, however, the over-all sensory effect created by the perfume composition will be at least the sum total of the effects of each of the ingredients. Thus, the product produced according to the process of our invention can be used to alter, modify or enhance the aroma characteristics of a perfume composition, for example, by utilizing or moderating the olfactory reaction contributed by another ingredient in the composition.

The amount of composition produced by means of hydrogenation of the camphene-catechol reaction product which will be effective in perfume compositions as well as in perfume articles and colognes depends on many factors including the other ingredients, their amounts and the effects which are desired. If has been found that perfume compositions containing as little as 0.01% of reaction product produced using the process intermediate of our invention or even less (e.g. 0.005%) can be used to impart an intense sandalwood, musky, woody aroma to perfumes, soaps, cosmetics, colognes, detergents or other products. The amount employed can range up to 100% of the fragrance components and will depend on consideration of costs, nature of the end product, the effect desired on the finished product and the particular fragrance sought.

The composition produced by hydrogenating the intermediate cyclohexane diol derivatives of our invention is useful, taken along or in perfume compositions as an olfactory component for use in detergents and soaps; space odorants and deodorants; perfume; colognes; tiolet water; bath preparations; such as bath oils, and bath solids; hair preparations, such as lacquers, brilliantines, pomades and shampoos; cosmetic preparation, such as creams, deodorants, hand lotions and sun screens; powders, such as talcs, dusting powders, face powders and the like. When used as an olfactory component, as little as 1% of the composition produced by means of hydrogenation of the intermediate of our invention will suffice to impart an intense sandalwood note to sandalwood and woody type formulations. Generally, no more than 3% of the composition produced by means of hydrogenation of the intermediate of our invention (based on the ultimate end product) is required in the perfume composition.

In addition, such perfume composition or fragrance composition can contain a vehicle, or carrier for the composition produced by means of hydrogenation of the intermediate of our invention. The vehicle can be a liquid such as an alcohol, (necessarily a non-toxic alcohol), a non-toxic glycol, or the like. The carrier can also be absorbent solid, such as a gum (e.g. gum arabic) or components for encapsulating the composition (such as gelatin).

It will thus be apparent that the composition produced by means of hydrogenation of the intermediate of our invention can be utilized to alter, modify or enhance the aroma of perfume compositions, perfumed articles and colognes.

Examples I-XVII serve to illustrate processes for producing the products useful in our invention.

It will be understood that these Examples are illustrative and the invention is to be considered restricted thereto only as indicated in the appended claims.

All parts and percentages given herein are by weight unless otherwise specified.

EXAMPLE I

REACTION OF CAMPHENE AND CATECHOL

(BF$_3$-ETHERATE CATALYST)

Into a 1 liter reaction flask equipped with stirrer, thermometer, reflux condenser, dropping funnel, and heating mantle are placed:

| | |
|---|---|
| Catechol | 188 g |
| Toluene | 110 g |
| Boron trifluoride etherate | 16 g |

The resulting mixture is heated to 45° C.

Placed in a dropping funnel are the following ingredients:

| | |
|---|---|
| Camphene | 136 g |
| Toluene | 150 g |

The camphene-toluene solution is added to the catechol-toluene-boron trifluoride-etherate mixture over a period of two hours while maintaining the reaction mass at 45° C. The reaction mass is then heated to 95° C. and maintained at that temperature with stirring for an additional 12 hour period. 100 g of 5% sodium hydroxide are then added to the reaction mass followed by the stirring of the reaction mass for a period of 15 minutes. The reaction mass is then separated and the organic layer is washed neutral. Solvent is then stripped off yielding 343 g of an oil.

The resulting oil is rushed-over yielding the following fractions:

| Fraction Number | Vapor Temperature | Liquid Temperature | Pressure mm Hg | Weight of Fraction |
|---|---|---|---|---|
| 1 | 110–170° C | 164–200° C | 2.3 | 10.7 gm |
| 2 | 210 | 214 | 2.3 | 10.2 |
| 3 | 210 | 215 | 2.3 | 9.8 |
| 4 | 215 | 215 | 2.3 | 12.0 |
| 5 | 215 | 215 | 2.3 | 23.0 |
| 6 | 215 | 220 | 2.3 | 20.3 |
| 7 | 214 | 225 | 2.7 | 21.9 |
| 8 | 240 | 250 | 2.3 | 30.0 |
| 9 | 245 | 250 | | 27.2 |
| 10 | 245 | 28 | 2.3 | 2.5 |

Fractions 2–7 are bulked.

EXAMPLE II

HYDROGENATION OF REACTION PRODUCT OF CATECHOL AND CAMPHENE

Into a 1 liter autoclave is placed the following materials:

| | |
|---|---|
| Reaction product of catechol and camphene produced according to Ex. I (fractions 2–7) | 250 g |
| Isopropyl alcohol | 100 ml |
| Raney nickel | 15 g |

After sealing, the autoclave is then purged with nitrogen followed by hydrogen, and heated to 220° C. under 450 psi hydrogen pressure. While maintaining the autoclave pressure between 450 and 500 psig and stirring at a rate of 1200 rpm, the autoclave is periodically repressurized with hydrogen over a period of 16 hours. At the end of the 16 hour period, the reaction mass is removed from the autoclave and filtered. The autoclave is rinsed with two 200 g portions of isopropyl alcohol. The isopropyl alcohol is then stripped from the reaction mass and the resulting material (240 g) is distilled on an 8" vigreaux column yielding the following fractions:

| Fraction Number | Vapor Temperature | Liquid Temperature | Pressure mm Hg | Weight of Fraction |
|---|---|---|---|---|
| 1 | 95–120° C | 151–174° C | 2.5 | 16.2 gm |
| 2 | 156 | 186 | 2.5 | 11.3 |
| 3 | 175 | 196 | 2.5 | 17.0 |
| 4 | 175 | 194 | 2.5 | 19.7 |
| 5 | 182 | 197 | 2.5 | 19.6 |
| 6 | 184 | 197 | 2.5 | 30.7 |
| 7 | 187 | 200 | 2.5 | 29.9 |
| 8 | 167 | 197 | 2.5 | 24.7 |

-continued

| Fraction Number | Vapor Temperature | Liquid Temperature | Pressure mm Hg | Weight of Fraction |
|---|---|---|---|---|
| 9 | 172 | 207 | 2.5 | 26.6 |
| 10 | 170 | 250 | 2.5 | 17.3 |

Fractions 2-9 are bulked and the resulting product has a strong sandalwood aroma; about five-ten times as strong as that product produced according to Example II or Example V of U.S. Pat. No. 3,499,937.

The resulting product is a mixture of several chemical compounds.

EXAMPLE III

FLORAL-WOODY FORMULATION

The following mixture is produced:

| Ingredients | Parts by Weight |
|---|---|
| Rhodinol | 40 |
| Phenylethyl alcohol | 60 |
| Linalol | 20 |
| Bergamot oil | 30 |
| Hydroxycitronellal | 110 |
| Alpha-amylcinnamic aldehyde | 30 |
| p-isopropyl-alpha-methyl phenyl-propyl-aldehyde (10% in ethyl alcohol) | 45 |
| Undecylaldehyde (10% in ethyl alcohol) | 45 |
| Benzyl acetate | 75 |
| Indol (10% in ethyl alcohol) | 15 |
| Undecalactone (1% in ethyl alcohol) | 30 |
| Ylang | 20 |
| Eugenol | 10 |
| Methylionone | 90 |
| Vetiver acetate | 30 |
| Product produced according to Ex. II | 6 |
| Musk ketone | 60 |
| Heliotropin | 40 |
| Coumarin | 20 |
| Natural Civet (10% in ethyl alcohol) | 25 |
| Orange absolute | 30 |
| Jasmin absolute | 35 |
| Rose absolute | 30 |

The product produced according to Example II adds an intense sandalwood note to this floral woody formulation using a concentration of the product of Example II which is 1/5 to 1/10 that required when using the product of Example II or Example V of U.S. Pat. No. 3,499,937.

EXAMPLE IV

PREPARATION OF A COSMETIC AND POWDER COMPOSITION

A cosmetic powder is prepared by mixing in a ball mill, 100 g of talcum powder with 0.25 g of the composition produced by means of hydrogenation of the reaction product of camphene and catechol prepared according to Example II. It has an excellent sandalwood aroma with woody and musky notes. By the same process a cosmetic powder is prepared by mixing in a ball mill, 100 g of talcum powder with 1 g of the perfume composition prepared according to Example III. It, too, has an excellent sandalwood aroma with woody and musky nuances.

EXAMPLE V

PERFUMED LIQUID DETERGENT

Concentrated liquid detergents with intense sandalwood aromas are prepared containing 0.10%, 0.15% and 0.20% of the composition produced by means of the hydrogenation of the reaction product of camphene and catechol prepared according to Example II. The detergents are prepared by adding and homogeneously mixing the appropriate quantity of hydrogenation product (of reaction product of catechol and camphene) in the liquid detergent. The detergents all posses intense sandalwood aromas, with the intensity increasing with greater concentrations of hydrogenation product.

EXAMPLE VI

PREPARATION OF A COLOGNE AND HANDKERCHIEF PERFUME

The composition produced by means of hydrogenation of the reaction product of camphene and catechol prepared according to the process of Example II is incorporated into a cologne at a concentration of 2.5% in 85% aqueous ethanol; and into a handkerchief perfume at a concentration of 20% (in 95% aqueous ethanol). A distinct and definite sandalwood fragrance with musky and woody nuances is imparted to the cologne and to the handkerchief perfume.

EXAMPLE VII

PREPARATION OF A SOAP COMPOSITION

One hundred grams of soap chips are mixed with one grams of the composition produced by means of hydrogenation of the reaction product of catechol and camphene produced according to Example II until a substantially homogeneous composition is obtained. The perfumed soap composition manifests an excellent sandalwood, woody, musky aroma. A similar aroma is created by adding three grams of the perfume composition of Example III to the soap chips and mixing until a homogenous composition is obtained. The resulting perfumed soap composition manifests an excellent sandalwood aroma.

EXAMPLE VIII

REACTION OF CAMPHENE AND CATECHOL (USING $H_2SO_4$ CATALYST)

Into a 1 liter reaction flask equipped with stirrer, thermometer, reflux condenser, dropping funnel and heating mantle are placed:

| | |
|---|---|
| Catechol | 330 g |
| Concentrated Sulfuric Acid (95%) | 0.4 g |

The resulting mixture is heated to 120° C. Placed in a dropping funnel fitted with a heating tape is 375 g of molten camphene. The molten camphene is added to the catechol-sulfuric acid mixture over a period of six (6) hours while maintaining the reaction mass at 120° C. At the end of the six (6) hour period, the reaction mass is stirred at 120° C. for another two hours. 0.5 g of sodium hydroxide dissolved in 1 gm water is then added, followed by the stirring of the reaction mass for a period of 15 minutes.

The resulting crude product is then rushed-over yielding the following fractions:

| Fraction Number | Vapor Temperature | Liquid Temperature | Pressure mm Hg | Weight of Fraction |
|---|---|---|---|---|
| 1 | 120–140° C | 147–160° C | 3.0 | 23.3 gm |
| 2 | 140 | 165 | 3.0 | 45.7 |
| 3 | 75 | 204 | 3.0 | 40.2 |
| 4 | 210 | 215 | 3.0 | 51.8 |
| 5 | 210 | 215 | 3.0 | 38.8 |
| 6 | 212 | 220 | 3.0 | 47.2 |
| 7 | 215 | 224 | 3.0 | 41.2 |
| 8 | 222 | 230 | 3.0 | 45.6 |
| 9 | 236 | 254 | 3.0 | 39.9 |
| 10 | 230 | 260 | 6.0 | 29.8 |

Fractions 4–9 are bulked.

EXAMPLE IX

HYDROGENATION OF REACTION PRODUCT OF CATECHOL AND CAMPHENE OF EXAMPLE VIII

Into a 1 liter autoclave is placed the following materials:

| | |
|---|---|
| Reaction product of catechol and camphene produced according to Ex. VIII (fractions 2–8) | 350 g |
| Isopropyl alcohol | 100 ml |
| Raney nickel | 30 g |

After sealing, the autoclave is purged with nitrogen followed by hydrogen, and then heated to a temperature in the range of 225–230° C. at a pressure of 500 psig. The autoclave is operated at this set of conditions for three hours. After the three hour period the autoclave pressure rises to about 850 psig and the autoclave is periodically vented back to 500 psig for a period of 12 hours.

At the end of the 12 hour period, the reaction mass is removed from the autoclave and and filtered. The autoclave is then rinsed with two 200 g portions of isopropyl alcohol. The isopropyl alcohol is then stripped from the reaction mass and the resulting material is distilled on an 10" vigreaux column yielding the following fractions:

| Fraction Number | Vapor Temperature | Liquid Temperature | Pressure mm Hg | Weight of Fraction |
|---|---|---|---|---|
| 1 | 80–116° C | 148–150° C | 2.5 | 4.4 gm |
| 2 | 135 | 155 | 2.5 | 10.1 |
| 3 | 140 | 156 | 2.5 | 12.3 |
| 4 | 145 | 160 | 2.5 | 12.2 |
| 5 | 148 | 160 | 2.5 | 24.5 |
| 6 | 150 | 164 | 2.5 | 31.1 |
| 7 | 154 | 167 | 2.5 | 30.0 |
| 8 | 157 | 173 | 2.5 | 31.3 |
| 9 | 162 | 181 | 2.5 | 31.6 |
| 10 | 168 | 189 | 2.5 | 26.5 |
| 11 | 181 | 215 | 2.5 | 29.4 |
| 12 | 182 | 224 | 2.5 | 17.8 |
| 13 | 194 | 257 | 2.5 | 29.5 |
| 14 | 231 | 274 | 2.5 | 32.6 |
| 15 | 239 | 290 | 2.5 | 8.4 |

Fractions 6–10 are bulked. The resulting product has a strong sandalwood aroma, with woody nuances; approximately 5–10 times the strength of the product produced according to the processes of Example II or Example V of U.S. Pat. No. 3,499,937.

The resulting product is a mixture of several chemical compounds. The GLC profile thereof is set forth in FIG. 1. (Conditions 2% carbowax-coated 18' by ¼" column, programmed at 80–220° C.).

EXAMPLE X

FLORAL-WOODY FORMULATION

The following mixture is prepared:

| Ingredients | Parts by Weight |
|---|---|
| Rhodinol | 40 |
| Phenylethyl alcohol | 60 |
| Linalol | 20 |
| Bergomot oil | 30 |
| Hydroxycitronellal | 110 |
| Alpha-amylcinnamic aldehyde | 30 |
| p-isopropyl-alpha-methyl phenyl-propyl-aldehyde (10% in ethyl alcohol) | 45 |
| Undecylaldehyde (10% in ethyl alcohol) | 45 |
| Benzyl acetate | 75 |
| Indol (10% in ethyl alcohol) | 15 |
| Undecalactone (1% in ethyl alcohol) | 30 |
| Ylang | 20 |
| Eugenol | 10 |
| Methylionone | 90 |
| Vetiver acetate | 30 |
| Product produced according to Ex. IX | 6 |
| Musk ketone | 60 |
| Heliotropin | 40 |
| Coumarin | 20 |
| Natural Civet (10% in ethyl alcohol) | 25 |
| Orange absolute | 30 |
| Jasmin absolute | 35 |
| Rose absolute | 30 |

The product produced according to Example IX adds the intense sandalwood note to this floral woody formulation using a concentration of the product of Example IX which is 1/5–1/10 that of the product produced according to the processes of Example II or Example V of U.S. Pat. No. 3,499,937.

EXAMPLE XI

REACTION OF CAMPHENE AND CATECHOL (USING A "FILTROL ®" CATALYST)

Into a 1 liter reaction flask equipped with stirrer, thermometer, reflux condenser, dropping funnel, and heating mantle are placed:

| | |
|---|---|
| Catechol | 330 g |
| Filtrol ® 24 (A 20–60 mesh acid clay manufactured by the Filtrol Corporation of Los Angeles, California and having the following properties: | 33 g |
| Particle-Size Analysis by Tyler Standard Sieve | |
| Through 20 Mesh, Wt. % | 100 |
| Through 60 Mesh, Wt. % | 5 |
| Free Moisture, Wt. % | 10 |
| Free & Combined Moisture, Wt. % (Loss at 1700° F) | 15 (max.) |
| Bulk Density, lbs./cu.ft. | 47 |
| Particle Density | 1.3 |
| Surface Area, $N^2$ adsorption (BET Method) sq. M/gm | 280–300 |

The resulting mixture is heated to 150° C. 408 g of molten camphene are then placed in a dropping funnel fitted with a heating tape. The molten camphene is added to the catecholFiltrol ® mixture over a period of six (6) hours while maintaining the reaction mass at 150°–155° C. At the end of the six (6) hour period, the reaction mass is stirred for an additional four (4) hours at 150° C. The reaction mass is rushed-over yielding the following fractions:

| Fraction Number | Vapor Temperature | Liquid Temperature | Pressure mm Hg | Weight of Fraction |
|---|---|---|---|---|
| 1 | 100–150° C | 150–170° C | 3.0 | 46.2 gm |
| 2 | 175 | 204 | | 21.4 |
| 3 | 186 | 215 | 3.5 | 42.2 |
| 4 | 198 | 205 | 2.5 | 49.5 |
| 5 | 205 | 209 | 2.5 | 53.2 |
| 6 | 208 | 212 | 2.5 | 51.6 |
| 7 | 210 | 215 | 2.5 | 50.5 |
| 8 | 211 | 217 | 2.5 | 45.1 |
| 9 | 211 | 218 | 2.5 | 51.7 |
| 10 | 215 | 218 | 2.5 | 54.0 |
| 11 | 218 | 230 | 2.5 | 49.3 |
| 12 | 223 | 240 | 2.5 | 39.3 |
| 13 | 210 | 245 | 3.8 | 28.9 |
| 14 | 230 | 280 | 5.0 | 27.1 |
| 15 | 250 | 320 | 3.8 | 28.7 |

EXAMPLE XII

HYDROGENATION OF REACTION PRODUCT OF CATECHOL AND CAMPHENE

Into a 1 liter autoclave is placed the following materials:

| | | |
|---|---|---|
| Reaction product of catechol and camphene produced according to Ex. XI (fractions 3–13) | 400 g | |
| Isopropyl alcohol | 100 ml | |
| Raney nickel | 30 g | |

After sealing, the autoclave is then purged with nitrogen followed by hydrogen. The autoclave is then heated to 155° C. under 500 psig hydrogen pressure and kept at 155°–197° C. for about 1 hour at which time the hydrogen uptake diminishes considerably. The reaction mass is then heated to between 220° C. and 235° C. and the autoclave pressure builds up to about 900 psig. The autoclave is periodically vented down to 500 psig over a period of 11 hours while maintaining the temperature at 220° C.–235° C. At the end of the 11 hour period, the reaction mixture is cooled to 110° C. at which temperature it is stirred for a period of about 5 hours during which time significant hydrogen uptake is observed. The reaction mass is then removed from the autoclave, filtered and the isopropanol is recovered at atmospheric pressure to 100° C., then at 20 mm Hg at 100° C. 11 grams of Primol ® is added to the resulting oil. The resulting oil is then distilled on an 8″ vigreaux column yielding the following fractions:

| Fraction Number | Vapor Temperature | Liquid Temperature | Pressure mm Hg | Weight of Fraction |
|---|---|---|---|---|
| 1 | 44–100° C | 120–155 | 2.5 | 8.0 gm |
| 2 | 140 | 160 | 2.5 | 16.0 |
| 3 | 146 | 163 | 2.5 | 17.8 |
| 4 | 150 | 165 | 2.5 | 22.0 |
| 5 | 155 | 165 | 2.5 | 25.0 |
| 6 | 157 | 167 | 2.5 | 26.8 |
| 7 | 159 | 169 | 2.5 | 27.5 |
| 8 | 160 | 171 | 2.5 | 31.2 |
| 9 | 165 | 177 | 2.5 | 28.0 |
| 10 | 170 | 185 | 2.5 | 32.5 |
| 11 | 172 | 190 | 2.5 | 23.2 |
| 12 | 187 | 207 | 2.5 | 19.7 |
| 13 | 195 | 214 | 2.5 | 26.0 |
| 14 | 203 | 219 | 2.5 | 24.9 |
| 15 | 225 | 308 | 2.5 | 12.3 |

Fractions 5–10 are bulked and the resulting product has a strong sandalwood aroma with woody nuances; approximately 5–10 times the strength of the product which is produced according to the processes of Example II or Example IV of U.S. Pat. No. 3,499,937.

Figure 2:
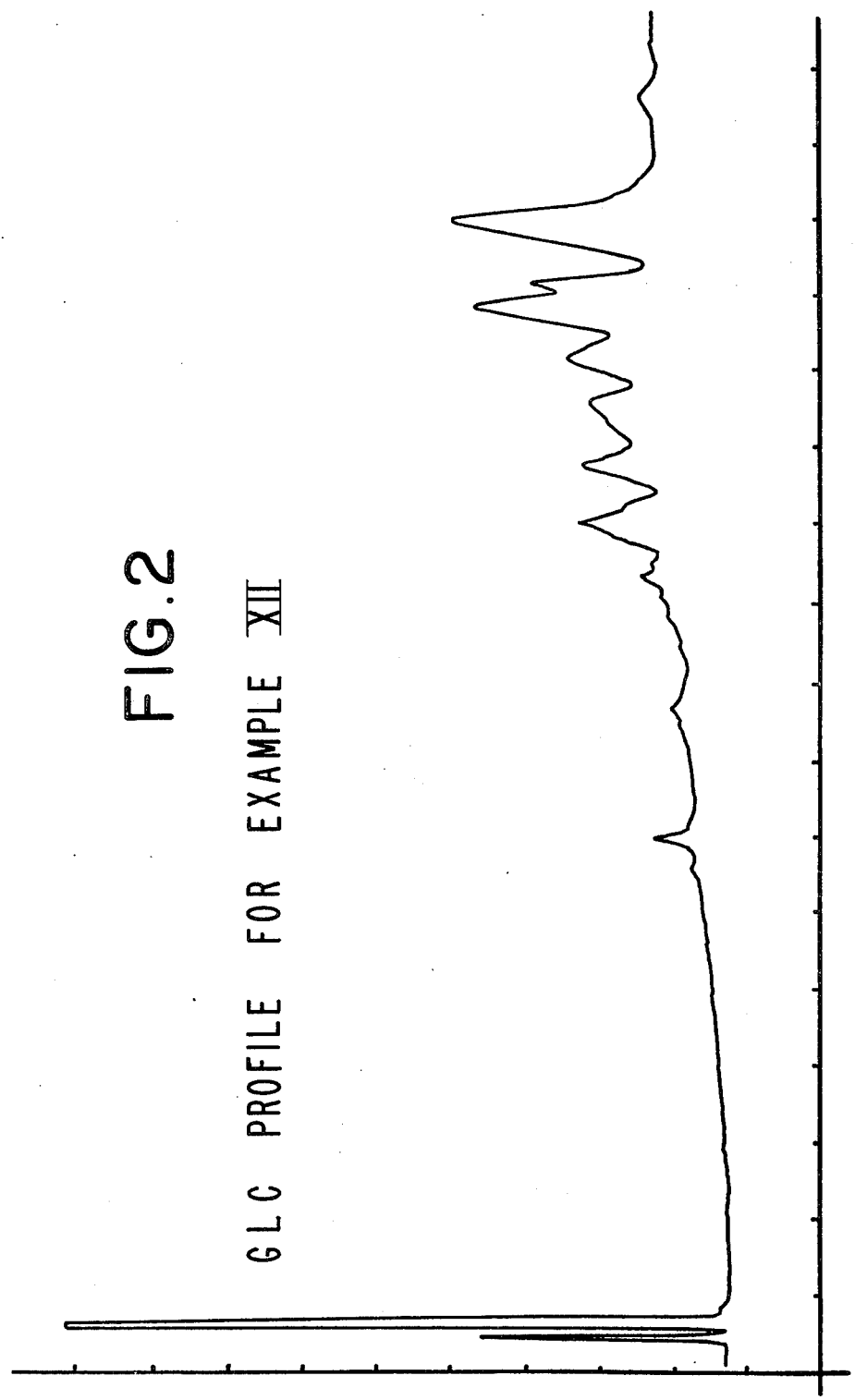
FIG. 2 is the GLC profile of the reaction product of Example XII.

The resulting product is a mixture of several chemical compounds. The GLC profile thereof is set forth in FIG. 2.

EXAMPLE XIII

HYDROGENATION OF REACTION PRODUCT OF CATECHOL AND CAMPHENE IN TWO STAGES: (A) STAGE 1 PRODUCT: DIOL MIXTURE; (B) STAGE 2 PRODUCT: ODIFEROUS MONOHYDROXY COMPOUND MIXTURE

Figure 3:
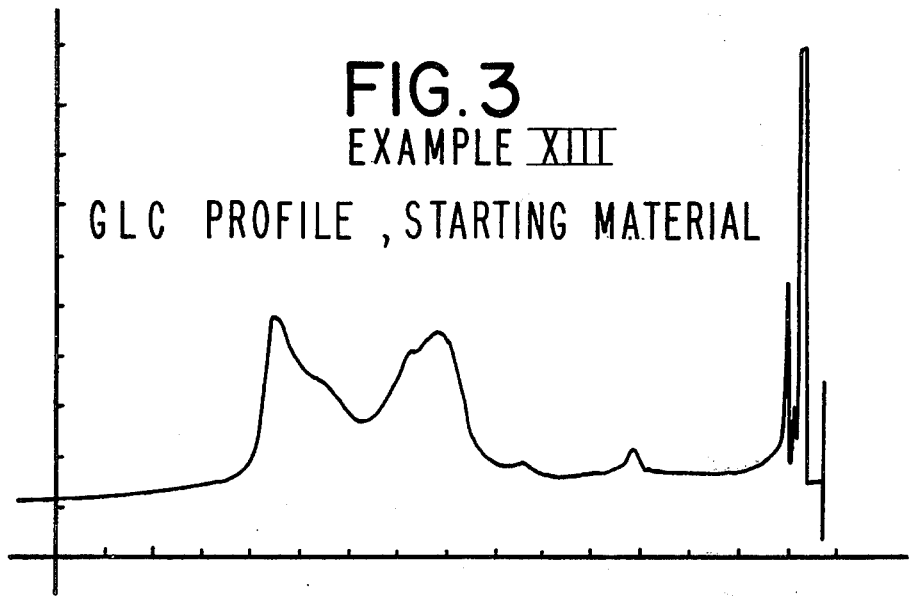
FIG. 3 is the GLC profile of the starting material (reactant to be hydrogenated) for use in the process of Example XIII.

STAGE 1:

Into a 1 liter autoclave is placed the following materials:

| | |
|---|---|
| Reaction product of catechol and camphene produced according to Ex. XI (Fractions 3–13) (GLC Profile of this material is set forth in Fig. 3) | 397 g |
| Isopropyl Alcohol | 100 ml |
| Raney Nickel | 30 g |

After sealing, the autoclave is then purged with nitrogen followed by hydrogen. The autoclave is pressurized with hydrogen to 500 psig and heated to 100° C., at which temperature stirring is commenced. The autoclave is then heated up to a temperature of less than 160° C. for the major portion of the time of the 1st stage of hydrogenation. However, as the uptake of hydrogen diminishes, the autoclave is heated to a temperature of 205° C. A table showing the time, temperature of hydrogenation, autoclave pressure, reservoir pressure, pressure drop and total pressure drop is set forth below:

| Time | Temperature | Autoclave | Reservoir Pressure | Pressure Drop | Total Pressure Drop |
|---|---|---|---|---|---|
| | | (psig) | (psig) | (psig) | (psig) |
| 0920 | 75° C | 500 | 2010 | | |
| 0947 | 110 | 540 | 2010 | | |
| 0952 | 125 | 340 | 2010 | | |
| 1017 | 110 | 500 | 850 | 1160 | 1160 |
| 1030 | 125 | 500 | 580 | 170 | 1430 |
| 1030 | 125 | 500 | 2010 | — | |
| 1045 | 145 | — | — | — | — |
| 1055 | 180 | 500 | 600 | 1410 | 2840 |
| 1055 | 180 | 480 | 2010 | — | — |
| 1205 | 160 | 500 | 680 | 1330 | 4170 |
| 1205 | 160 | 480 | 2000 | — | |
| 1240 | 170 | 480 | 1620 | 380 | 4550 |
| 1317 | 195 | 480 | 1430 | — | |
| 1533 | 205 | 500 | 1130 | — | |
| 1616 | 205 | 480 | 1120 | 500 | 5050 |
| 1920 | 90 | 150 | | | |

At the end of the period of 10 hours as is set forth in the above table, the autoclave is opened and the reaction mass is filtered. The autoclave is then rinsed twice with isopropyl alcohol. The solvent is stripped off at 110° C. and atmospheric pressure, then at 25 mm Hg at 110° C. At this point IR and GLC analysis indicates that the reaction mass is a mixture of compounds represented by the structures:

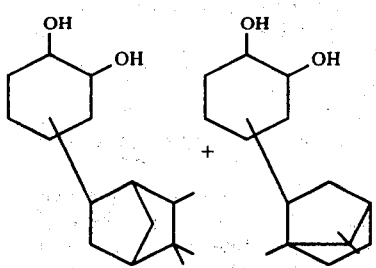

Figure 4:
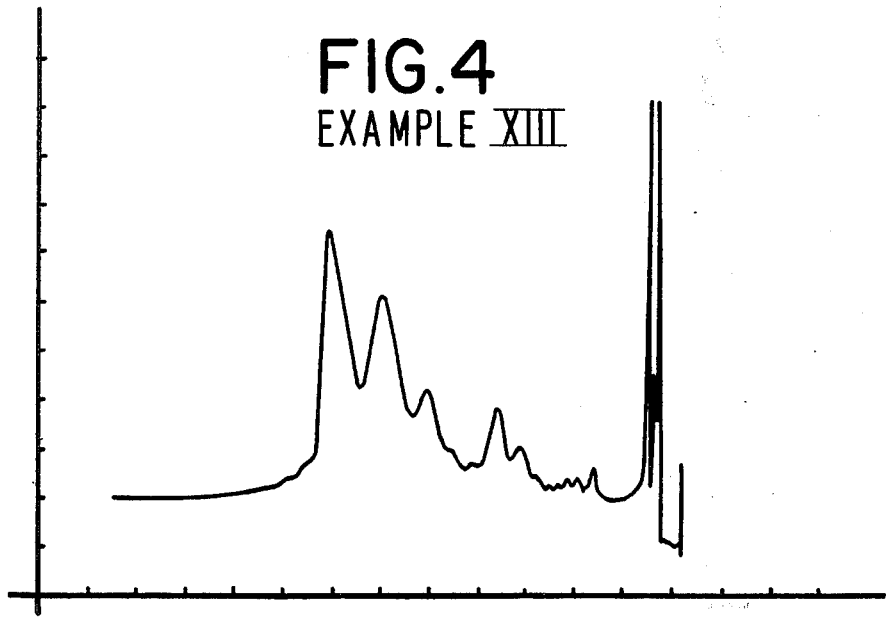
FIG. 4 is the GLC profile of the reaction product resulting from carrying out the first stage of the reaction of Example XIII.

The GLC profile for the reaction mass existing at the end of Stage 1 is set forth in FIG. 4. The infra red spectrum for the compounds having the structure as above, is set forth in FIG. 4a.

The resulting material at the end of Stage 1 has no odor.

STAGE 2:

The solvent-stripped reaction product of the first stage of hydrogenation is admixed with 30 g of Raney nickel and 100 g of isopropyl alcohol and replaced into the 1 liter autoclave. After sealing, the autoclave is purged with nitrogen followed by hydrogen. The autoclave is then heated to 217° C. and held at 225°-230° C. and 500 psig for a period of eight hours. At the end of the eight hour period, the reaction mixture is cooled, the autoclave is opened and the reaction mass is removed from the autoclave, filtered and the isopropanol recovered at atmospheric pressure at 100° C., then at 25 mm Hg at 110° C. 19.5 g of Primol ® is added to the resulting oil which is then distilled on a 6" vigreaux column yielding the following fractions:

| Fraction Number | Vapor Temperature | Liquid Temperature | Pressure mm Hg | Weight of Fraction |
|---|---|---|---|---|
| 1 | 113° C | 148 | 2.3 | 4.9 |
| 2 | 146 | 165 | 3.5 | 17.4 |
| 3 | 139 | 165 | 2.7 | 12.4 |
| 4 | 145 | 170 | 2.7 | 11.6 |
| 5 | 147 | 175 | 2.7 | 14.0 |
| 6 | 154 | 175 | 2.7 | 15.5 |
| 7 | 158 | 178 | 2.7 | 16.7 |
| 8 | 165 | 178 | 2.5 | 22.7 |
| 9 | 165 | 185 | 2.8 | 15.8 |
| 10 | 156 | 183 | 2.4 | 21.4 |
| 11 | 162 | 187 | 2.4 | 22.1 |
| 12 | 172 | 192 | 2.4 | 26.0 |
| 13 | 187 | 204 | 2.3 | 18.2 |
| 14 | 209 | 236 | 2.5 | 21.9 |
| 15 | 235 | 250 | 2.7 | 20.5 |
| 16 | 241 | 250 | 2.7 | 8.6 |

Fractions 6–14 are bulked and the resulting product has a strong sandalwood aroma with woody nuances; approximately 5–10 times the strength of the product which is produced according to the products of Example II and Example V of U.S. Pat. No. 3,499,937.

Figure 5:
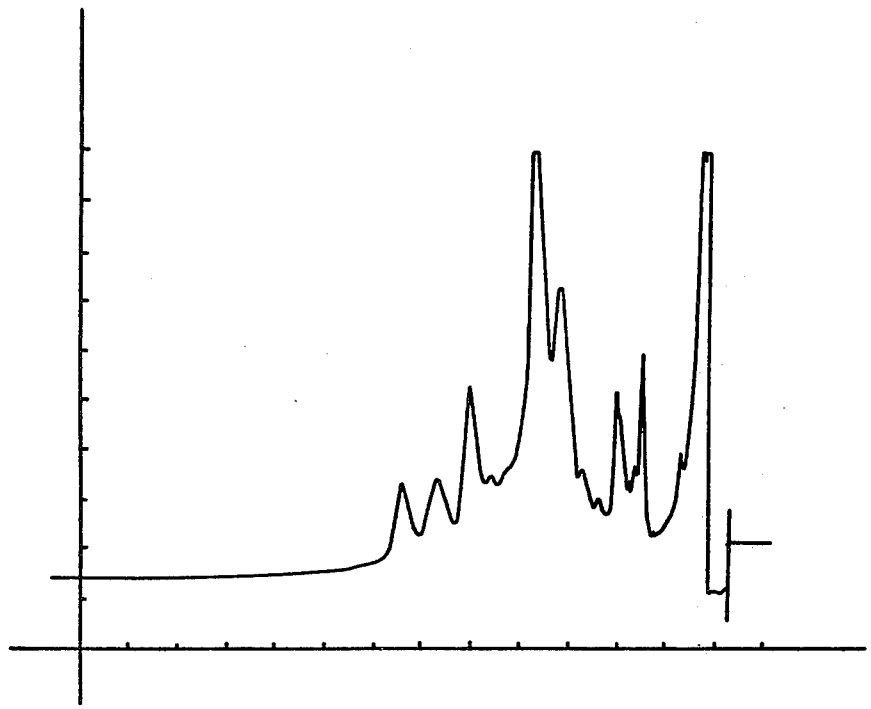
FIG. 5 is the GLC profile of the reaction product formed as a result of carrying out the second stage of the reaction of Example XIII.

The resulting product is a mixture of several chemical compounds. The GLC profile thereof is set forth in FIG. 5.

EXAMPLE XIV

PREPARATION OF A COSMETIC AND POWDER COMPOSITION

A cosmetic powder is prepared by mixing in a ball mill, 100 g of talcum powder with 0.25 g of the composition produced by means of hydrogenation of the reaction product of camphene and catechol prepared according to Example XIII, second stage. It has an excellent sandalwood aroma with woody and musky nuances.

EXAMPLE XV

PERFUMED LIQUID DETERGENT

Concentrated liquid detergents with intense sandalwood aromas are prepared containing 0.10%, 0.15% and 0.20% of the composition produced by means of the hydrogenation of the reaction product of camphene and catechol prepared according to Example XIII, second stage. The detergents are prepared by adding and homogeneously mixing the appropriate quantity of second stage hydrogenation product (of reaction product of catechol and camphene) in the liquid detergent. The detergents all posses intense sandalwood aromas, with the intensity increasing with greater concentrations of hydrogenation product.

EXAMPLE XVI

A low-phosphate spray-dried detergent composition is prepared according to Example III of Canadian Patent 1,014,814 containing the following materials:

| Component | Weight % |
|---|---|
| Surfactant System | 21.5% |
| Sodium linear alkyl benzene sulfonate wherein the alkyl group averages about 11.8 carbon atoms in length | 17.0% wt. ratio anionic/ nonionic = 3.8:1 |
| Condensation product of one mole of coconut fatty alcohol with about 6 moles of ethylene oxide | 4.5% |
| Sodium silicate (Na$_2$O/SiO$_2$ wt. ratio = 1:2.4) | 6.0% |
| Sodium silicate (Na$_2$O/SiO$_2$ wt. ratio = 1:2.0) | 6.0% |
| Sodium tripolyphosphate | 24.0% |
| Sodium sulfate | 35.3% |
| Sodium toluene sulfonate | 1.7% |
| Water | 4.0% |
| Reaction product of Example IX | 1.5% |

The resulting composition provides an excellent fabric laundering performance when employed under conventional home laundering conditions in a laundering liquor of 7 grains/gallon hardness with a composition concentration in laundering liquor of about 0.12% by weight. Not only does this material have a high sudsing performance but it has a very stable and intense sandalwood aroma. Such a composition is readily pourable and storage stable and is prepared with conventional spray-drying apparatus.

EXAMPLE XVII

A low-phosphate spray-dried detergent composition is prepared according to Example III of Canadian Patent 1,014,814 containing the following materials:

| Component | Weight % |
|---|---|
| Surfactant System | 21.5% |
| Sodium linear alkyl benzene sulfonate wherein the alkyl group averages about 11.8 carbon atoms in length | 17.0% wt. ratio anionic/ nonionic = 3.8:1 |
| Condensation product of one mole of coconut fatty alcohol with about 6 moles of ethylene oxide | 4.5% |
| Sodium silicate (Na$_2$O/SiO$_2$ wt. ratio = 1:2.4) | 6.0% |
| Sodium silicate (Na$_2$O/SiO$_2$ | |

| Component | Weight % |
| --- | --- |
| wt. ratio = 1:2.0) | 6.0% |
| Sodium tripolyphosphate | 24.0% |
| Sodium sulfate | 35.3% |
| Sodium toluene sulfonate | 1.7% |
| Water | 4.0% |
| Reaction product of Example XIII | 1.5% |

The resulting composition provides an excellent fabric laundering performance when employed under conventional home laundering conditions in a laundering liquor of 7 grains/gallon hardness with a composition concentration in laundering liquor of about 0.12% by weight. Not only does this material have a high sudsing performance but it has a very stable and intense sandalwood aroma. Such a composition is readily pourable and storage stable and is prepared with conventional spray-drying apparatus.

What is claimed is:

1. A process for producing a perfumed detergent composition comprising the step of intimately admixing with a solid or liquid detergent base from 1% up to 3% of a product produced by the process which comprises reacting catechol having the structure:

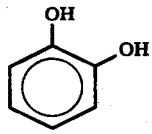

with camphene having the structure:

in the presence of a Friedel Crafts Catalyst to form a catecholcamphene alkylation product, recovering said alkylation product at a temperature in the range of from 186 up to 236° C. and at a pressure of from 2.3 up to 3.8 mm Hg, hydrogenating the said catechol-camphene alkylation product in the presence of a hydrogenation catalyst to form a hydrogenated catechol-camphene addition product and recovering the said hydrogenated catechol-camphene addition product at a temperature in the range of from 150° C. up to 172° C. and a pressure of about 2.5 mm Hg, the Friedel Crafts Catalyst being selected from the group consisting of boron trifluoride etherate, sulfuric acid, acid clay, aluminum trichloride, boron trifluoride, boron trifluoride-acetic acid, boron trifluoride-phosphoric acid, zinc chloride, aluminosilicate molecular sieve, and ferric chloride, the reaction between catechol and camphene being carried out at a temperature in the range of from about 120° C. up to 175° C. and the mole ratio of catechol to camphene being in the range of from about 0.5:1 up to about 4:1, the hydrogenation reaction being carried out within a temperature range of 100° C. up to 300° C., the latter portion of the reaction time being at from 200° up to 300° C.

2. A process for producing a perfumed detergent composition comprising the step of intimately admixing with a solid or liquid detergent base from 1% up to 3% of a product produced by the process which comprises reacting catechol having the structure:

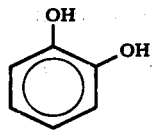

with camphene having the structure:

in the presence of a Friedel Crafts Catalyst to form a catechol-camphene alkylation product, recovering the said catechol-camphene alkylation product at a temperature of from 186° up to 236° C. and a pressure of from 2.3 up to 3.8 mm Hg hydrogenating the said catechol-camphene alkylation product in the presence of a hydrogenation catalyst to form a hydrogenated catechol-camphene addition product, the said hydrogenation being carried out in two consecutive stages:

(1) A first stage carried out at a temperature of from 100° C. up to 200° C.; and (2) A second stage carried out at a temperature of from 200° C. up to 300° C., said hydrogenated catechol-camphene addition product being recovered at a temperature in the range of from 154° up to 209° C. and a pressure of from 2.3 up to 2.8 mm Hg, the Friedel Crafts Catalyst being selected from the group consisting of boron trifluoride etherate, sulfuric acid, acid clay, aluminum trichloride, boron trifluoride, boron triflurodie-acetic acid, boron trifluoride-phosphoric acid, zinc chloride, aluminosilicate molecular sieve, and ferric chloride, the reaction between catechol and camphene being carried out at a temperature in the range of from 120° C. up to 175° C. and the mole ratio of catechol to camphene being in the range of from about 0.5:1 up to about 4:1.

* * * * *